US00PP10738P

United States Patent [19]

Olesen et al.

[11] Patent Number: Plant 10,738

[45] Date of Patent: Dec. 29, 1998

[54] MINIATURE ROSE PLANT NAMED 'POULRAT'

[75] Inventors: L. Pernille Olesen; Mogens N. Olesen, both of Fredensborg, Denmark

[73] Assignee: Poulsen Roser APS, Fredensborg, Denmark

[21] Appl. No.: 832,299

[22] Filed: Apr. 3, 1997

[51] Int. Cl.[6] ..... A01H 5/00

[52] U.S. Cl. ..... Plt./8.2

[58] Field of Search ..... Plt./8.2

[56] References Cited

PUBLICATIONS

UPOU–ROM, 1997/04, Plant Variety Database, GTI Jouve Retrieval Software, Citation for 'POULRAT'.

*Primary Examiner*—Howard J. Locker
*Attorney, Agent, or Firm*—Foley & Lardner

[57] ABSTRACT

A new and distinct cultivar of miniature rose plant named 'POULrat', characterized by its extreme compactness which is suitable for year-round forcing in glasshouses, thereby reducing or eliminating the need for application of plant growth regulators; good bud count for a compact variety; stable, non-fading yellow color; excellent disease resistance; attractive dark green foliage with semi-glossy finish; and limited numbers of thorns.

2 Drawing Sheets

The present invention comprises a new and distinct cultivar of rose plant of the miniature class, hereinafter referred to by the cultivar name 'POULrat'.

BACKGROUND OF THE INVENTION

'POULrat' is a product of a planned breeding program having the objective of creating new rose cultivars which are extremely compact, floriferous, with good shelf life, and which are suitable for year-round forcing in small pots in glasshouses. Such traits in combination were not previously present in available commercial cultivars of this type.

'POULrat' was originated from a hybridization made in a controlled breeding program in Fredensborg, Denmark in 1992. One parent was an unnamed seedling. The other present parent was 'POULsendo'.

The parent cultivar 'POULsendo' differs from 'POULrat' in a number of ways. The open flower of 'POULsendo' is larger, measuring 50 mm in diameter, than that of 'Poulrat', measuring 22 to 30 mm in diameter. The flowers of 'POULsendo' are double with 3 to 6 buds per flowering stem, while the flowers of 'POULrat' are singular with 1 to 4 buds per floweirng stem. 'POULsendo' grow to 30 to 45 cm in height and 30 to 40 cm in width while 'POULrat' grows to 20 to 25 cm in height and 18 to 22 cm in width.

'POULrat' was discovered and selected as one flowering plant within the progeny of the stated parentage by L. Pernille and Mogens N. Olesen, in June 1993 in a controlled environment in Fredensborg, Denmark.

Asexual reproduction of the new cultivar by budding and cutting, as performed initially by Pernille and Mogens Olesen in August 1993 at Fredensborg, Denmark, has demonstrated that the combination of characteristics, as herein disclosed for 'POULrat', are firmly fixed through successive generations of asexual reproduction.

'POULrat' has not been observed under all possible environmental conditions. The phenotype may vary significantly with variations in environment, such as temperature, light intensity, and day length, without a change in genotype of the variety. The following observations, measurements and comparisons describe the plants grown in Fredensborg, Denmark and Half Moon Bay, Calif. under greenhouse conditions which approximate those generally used in commercial practice.

BRIEF SUMMARY OF THE INVENTION

The following traits have been repeatedly observed and are determined to be basic characteris- tics of 'POULrat', which in combination, distinguish this rose as a new and distinct cultivar:

1. Extremely compact pot rose suitable for year- round forcing in glasshouses, thereby reducing or eliminating the need for application of plant growth regulators.
2. Good bud count for a compact variety.
3. Stable, non-fading yellow color.
4. Excellent disease resistance.
5. Attractive dark green foliage with semi-glossy finish.
6. Limited numbers of thorns.

Of the many commercial cultivars known to the present inventors, the most similar in comparison to 'POULrat' is 'POULvert', U.S. Plant No. 8,856; granted Aug. 9, 1994.

TABLE A

| Characteristic | 'POULrat' | 'POULvert' |
|---|---|---|
| Flower size | 22–30 mm | 40 mm |
| Flower color | RHS 8B<br>Yellow Group | RHS 5C<br>Yellow Group |
| Bud color<br>1/4 open | RHS 13B<br>Yellow Group | RHS 5C<br>Yellow Group |
| Appropriate pot size for forcing | 6 cm pots<br>(2 1/3") | 10–12 cm pots<br>(4–5") |

Table A compares certain characteristics of 'POULrat'to those same characteristics of 'POULvert'.

In general comparison to 'POULvert', 'POULrat' has smaller flowers, smaller leaves, shorter stems, and is more suitable for forcing in 6 cm pots in commercial culture.

BRIEF DESCRIPTION OF THE DRAWINGS

The accompanying color photographic drawings show typical inflorescence and foliage characteristics of 'POULrat', with the colors being as nearly true as possible with illustrations of this type.

Sheet 1 shows a side view of a potted plant.

Sheet 2 shows (1) a flower stem, (2) bud and flower, (3) petals, (4) bud, (5) stem and (6) leaves of 'POULrat'.

DETAILED BOTANICAL DESCRIPTION

In the following description, color references are made to The Royal Horticultural Society Colour ("R.H.S.") Chart. The color values were determined between in Fredensborg, Denmark.

Classification:

*Botanical.*—*Rosa hybrida.*

*Commercial.*—'POULrat'

Parentage:

*Male Parent.*—'POULsendo',

*Female Parent.*—Unnamed proprietary cultivar.

Plant:

*General appearance.*—Habit: Extremely compact. Growth: Dwarf, upright. Size: When grown as a 6 cm pot plant, the average height of the plant itself is 8 to 10 cm and the average width is 6 to 8 cm. When grown as a nursery plant on its own roots, the average plant height is 20 to 25 cm and the average width is 18 to 22 cm. Canes: Smooth Main stems: Dwarf, upright. Color is R.H.S. 138A. Rachis: Color is R.H.S. 147C. Thorns: In a 5 cm length of a flowering stem, an average of 3 thorns are present. Thorns are flexible, or nearly so, and grow up to 6 mm in length, needle shaped, thorns are nearly white on upper portion of stems and tan colored on lower portion of stems. Color is R.H.S. 145B. Branches: Ordinary.

*Foliage.*—Leaves Number: Mostly 5 leaflet leaves. Average abundance. Shape: Leaflets are ovate. Appearance: Medium glossy, margins serrated, leaflets generally flat. Color (top side): Mature leaves are medium green R.H.S. 147B, Green-Yellow Group, darker with use of growth regulator. Juvenile leaves are R.H.S. 138A. Color (bottom side): Mature leaves are medium green R.H.S. 147D, Green-Yellow Group. Juvenile leaves are 147D. Stipules: Present, well formed, to 11 mm from base to tip. Color is R.H.S. 147B. Other foliage characteristics: Mean petiole length is 10 mm. Mean entire leaf length is 65 mm. Mean width of entire leaf is 35 mm.

Flowers:

*Borne.*—Singularly or nearly so on short pedicels.

*Type of stems.*—Upright, with a limited pubescence present.

*Number of flowers* (*per stem*).—Generally, 1 to 4 buds per flowering stem.

*Quantity of blooms.*—Generally up to 5 to 7 blooms per plant.

*Buds.*—Peduncle length: 10–15 mm. Peduncle surface: Limited numbers of hairs present. Peduncle strength: Average. Bud shape: Globular. Bud color: R.H.S. 13 B of the Yellow Group, when bud is ¾ open. Receptacle color: R.H.S. 138A of the Green Group. Lighter in color than sepals. Receptacle shape: Funnel shaped. Small in size. Receptacle surface: Nearly smooth. Sepals color: Green R.H.S. 136. Sepals surface texture: Covered in fine hairs. Approximately half of the sepals have small foliaceous appendages.

*Blooms.*—small yellow flowers with slightly reflexed petals. Size: Open flowers are 22–30 mm in diameter. Petalage: Double to very double. Approximately 35 to 40 petals per flower. Petalage length: Length is 8–10 mm. Texture: Petal is smooth, with weak undulation at the edge. Shape: Open flowers are flat, when viewed from the side. When viewed from the top, open flowers are round. Color: Upperside: Medium yellow R.H.S. 8B, of the Yellow Group. Color fades slightly to R.H.S. 8C of the Yellow Group as flower opens. Base petal spots absent. Underside: Medium yellow R.H.S. 8B, of the Yellow Group.

*Keeping quality.*—Blooms last 14 days on plant and 11 days as a cut flower.

*Fragrance.*—Lightly fragrant.

*Reproductive organs.*—Stamens: Overall, similar in position in relationship to stigma. Filaments: Light green in color, broaden at base. Anthers: Yellow in color, upright, somewhat irregular. Pistils: Similar in position in relationship to stamens. Styles: Light to moderately pubescent. Ovaries: Inferior Disease resistance: The variety has demonstrated good resistance to Mildew, Blackspot, and Botrytis.

We claim:

1. A new and distinct cultivar of rose plant named 'POULrat', as illustrated and described.

* * * * *

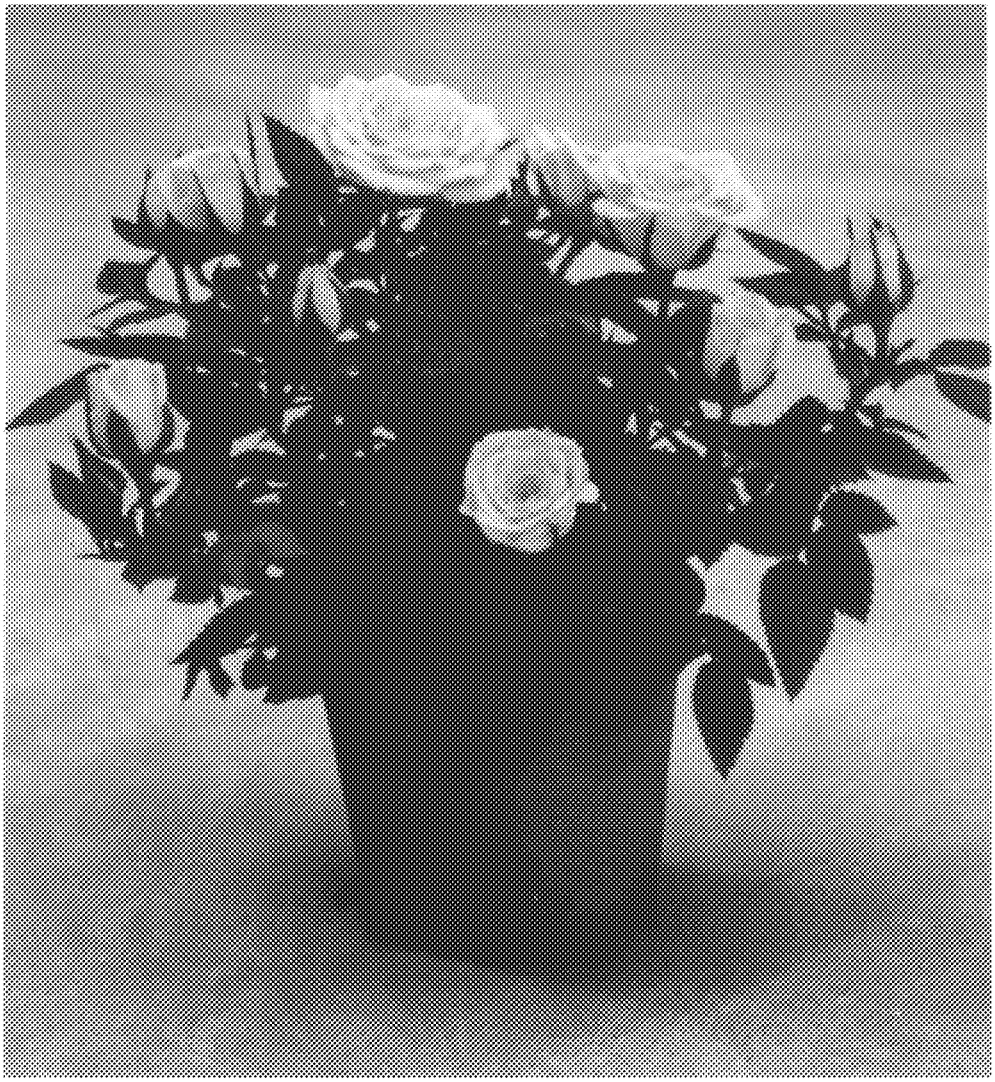

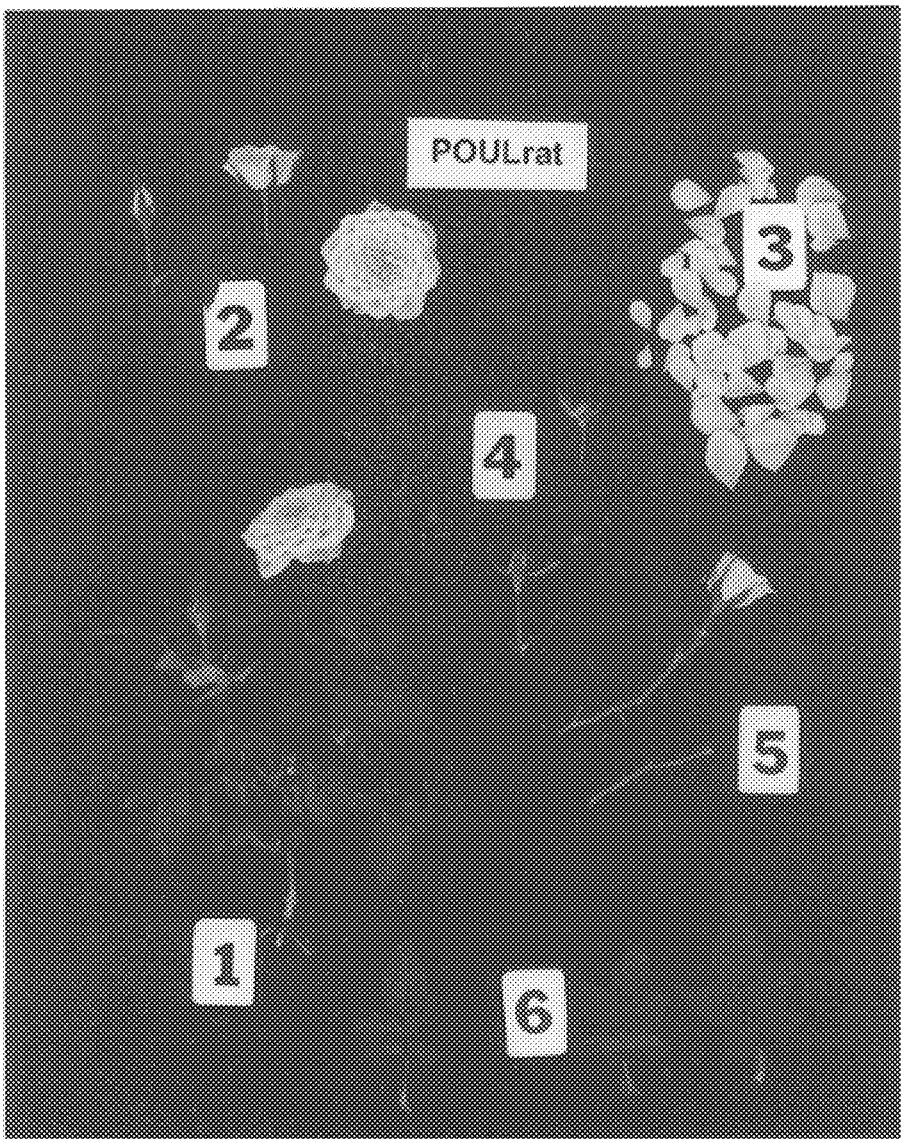
POULrat
1
2
3
4
5
6